United States Patent [19]

Bobowski et al.

[11] 4,261,890

[45] Apr. 14, 1981

[54] SUBSTITUTED TETRAHYDROBENZAZEPINES AND TETRAHYDRONAPHTHAZEPINES AND METHODS FOR THEIR PRODUCTION

[75] Inventors: George Bobowski, Ann Arbor, Mich.; Jeffrey M. Gottlieb, Morristown; John Shavel, Jr., Mendham, both of N.J.

[73] Assignee: Warner-Lambert Company, Morris Plains, N.J.

[21] Appl. No.: 14,795

[22] Filed: Feb. 26, 1979

[51] Int. Cl.$^3$ .................... C07D 223/14; A61R 31/55
[52] U.S. Cl. ............................. 260/239 BB; 424/244
[58] Field of Search .................................. 260/239 BB

[56] References Cited

U.S. PATENT DOCUMENTS 3,496,166   2/1970   Mull et al. ..................... 260/239 BB

*Primary Examiner*—Donald G. Daus
*Assistant Examiner*—David B. Springer
*Attorney, Agent, or Firm*—Stephen Raines

[57] ABSTRACT

Substituted tetrahydrobenzazepines and tetrahydronaphthazepines which are useful as pharmacological agents, especially in the treatment of cardiac arrhythmias, are disclosed. These compounds can be prepared by cyclizing an appropriately substituted ($\beta$-hydroxy-$\beta$-phenylethyl)($\beta$-phenylethyl)amine.

2 Claims, No Drawings

SUBSTITUTED TETRAHYDROBENZAZEPINES AND TETRAHYDRONAPHTHAZEPINES AND METHODS FOR THEIR PRODUCTION

SUMMARY AND DETAILED DESCRIPTION

The present invention relates to new substituted tetrahydrobenzazepines and tetrahydronaphthazepines. More particularly, the invention relates to new compounds of the formula

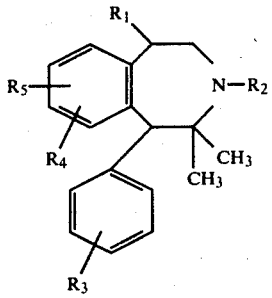

and acid addition salts thereof, and to a method for the production of the foregoing compounds; wherein $R_1$ is hydrogen, lower alkyl or phenyl, $R_2$ is hydrogen, lower alkyl or benzyl, $R_3$ is hydrogen, lower alkyl, chlorine or lower alkoxy, $R_4$ and $R_5$ are hydrogen, lower alkyl, lower alkoxy, chlorine, hydroxy, amino, lower alkylamino or di(lower alkyl)-amino and $R_4$ and $R_5$ taken together may constitute a fragment of the formula

—CH=CH—CH=CH—

The preferred compounds are those wherein $R_1$ and $R_2$ are hydrogen, $R_3$ is 3-methoxy, $R_4$ is 7-methoxy, $R_5$ is 8-methoxy and $R_1$ and $R_3$ are hydrogen, $R_2$ is methyl and $R_4$ and $R_5$ constitutes a —CH=CH—CH=CH— group at between the $C_8$ and $C_9$ positions. In addition, the invention also relates to certain intermediates.

The term "lower alkyl" is intended to mean an alkyl group of from one to six carbon atoms.

The term "lower alkoxy" is intended to mean "lower alkyl—O—."

The term "acid addition salts" is intended to mean salts formed by the addition of an acid. Typical salts are as follows: pamoate, acetate, citrate, hydrochloride, sulfate, phosphate, benzoate, etc. Pharmaceutically acceptable acid addition salts are preferred.

Certain of the compounds of this invention can exist in the form of stereoisomers, this invention is intended to encompass the specific isomers and the racemic mixtures. In addition, the invention is intended to include hydrates and solvates in the compounds of formula I.

Also, in accordance with the invention, the foregoing compounds of formula I can be prepared by cyclizing a compound of the formula

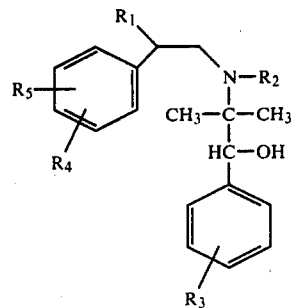

wherein $R_1$ through $R_5$ are as previously defined. The resulting compound may be isolated as a free base or a salt thereof by adjusting the pH. The cyclization is achieved by use of an acid catalyst at temperatures of from about 5° C. to about 175° C. for periods of from about one hour to about 60 hours, depending on the acid employed. For sulfuric acid, lower temperatures are preferred (5° C. to 35° C.); for methanesulfonic acid, intermediate temperatures are preferred (60° C. to 100° C.); while for polyphosphoric acid, higher temperatures are desired (80° C. to 175° C.). Solvent is not required for the above cyclizations although an inert organic solvent may be employed. Generally the acid is also used as the solvent.

Compounds of the formula II wherein $R_2$ is hydrogen are prepared by reducing compounds of the formula

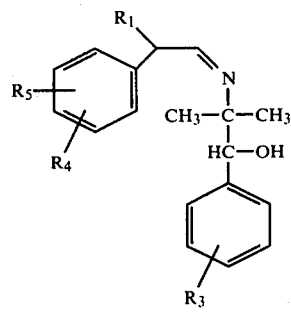

wherein $R_1$, $R_3$, $R_4$ and $R_5$ are as defined for formula I using an excess of potassium borohydride. The reaction is conducted in a solvent, such as methanol at a temperature of from about 15° C. to about 30° C. for from about ten to about thirty hours.

Compounds of formula III are prepared by condensing a compound of the formula

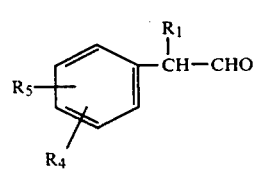

with a compound of the formula

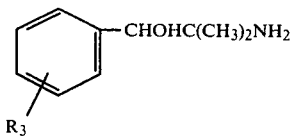

wherein $R_1$, $R_3$, $R_4$ and $R_5$ are as defined for formula I. Standard condensation procedures are employed, such as refluxing about equimolar quantities of the two reactants in benzene and azeotroping the water formed away from the reaction mixture using a Dean-Stark trap. The reaction time is a function of the time required for the theoretical amount of water to be collected in the trap for the reaction to have gone to completion. A general procedure is reported in U.S. Pat. No. 3,084,099, issued Feb. 2, 1963, which is incorporated by reference.

Many compounds of the formulae IV and V are known compounds, others are prepared by simple standard chemical procedures.

A second route to compounds of the formula II involves the reduction of compounds of the formula

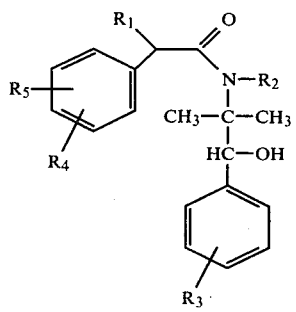

using lithium aluminum hydride or diborane. These standard reduction procedures are well documented in the literature. Generally an excess of reducing agent is employed in an inert solvent, such as tetrahydrofuran. The reaction temperature may vary from room temperature to the refluxing temperature of the solvent employed for periods of at least one hour.

Compounds of the formula IV are prepared by condensing a compound of the formula

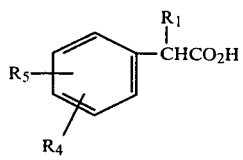

with the compound of the formula

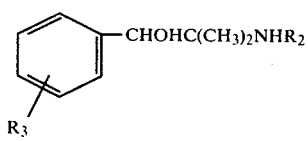

wherein $R_1$ through $R_5$ are as defined for formula I. This reaction is conducted by heating the two reactants together in approximately equimolar ratios in an inert solvent such as benzene in the presence of a water-absorbing agent or other means of removing water from the reaction mixture.

Many compounds of the formulae VII and VIII are known compounds, others are prepared by simple standard chemical procedures.

According to this invention, compounds of formula I wherein $R_1$, $R_3$, $R_4$ and $R_5$ are as defined for formula I and $R_2$ is lower alkyl or benzyl may be prepared by reacting a compound of the formula

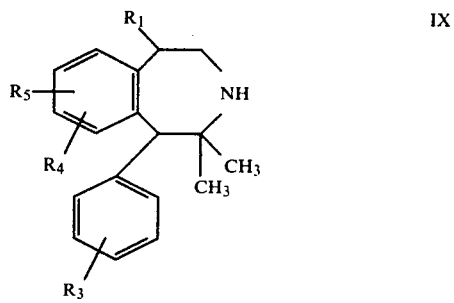

with a compound of the formula $R_2X$ or $(R_2O)_2SO_2$ wherein X is chloride, bromide or iodide. The reaction may be conducted at temperatures from about 0° C. to the refluxing temperature of the solvent (the size of the $R_2$ group will effect the reaction temperature) for periods of about one hour to about ten days. An inert organic solvent, such as tetrahydrofuran may be used.

Lastly, the compounds of formula IX wherein $R_2$ is methyl may be prepared by a standard reductive alkylation procedure using a formaldehyde-formic acid mixture. The reaction is generally conducted in an equeous solvent using excess formaldehyde and formic acid at the reflux temperature of the solvent for periods of from three to twenty-four hours.

The compounds of the invention are new chemical compounds of value as pharmacological agents. More specifically, the compounds are useful in treating cardiac arrhythmias and may be administered orally in the form of tablets, capsules, syrups, etc. or patenterally by being dissolved in an appropriate isotonic solution.

The effectiveness of the aforementioned compounds is determined in the standard ouabain-induced arrythmia screen as described in J. Pharm. Exp. Therapeutic, 175, 169 (1970), H. R. Kaplan and R. D. Robson and ibid, 145, 286–291 (1964). B. R. Lucchesi, and in the coronary ligated Harris dog [A. S. Harris, Circulation 1, 1318–1328, (1950)].

The compounds are generally active at about 3 to about 15 mg./kg. in the above mentioned tests. The preferred compounds being 2,3,4,5-tetrahydro-7,8-dimethoxy-1-(3-methoxyphenyl)-2,2-dimethyl-3-benzazepine hydrochloride and 2,3,4,5-tetrahydro-3,4,4-trimethyl-5-phenyl-1H-naphth-[1,2]azepine which are active at about 3 mg./kg. in ouabain-induced arrythmia test and 10 mg./kg. in the coronary ligated Harris dog test.

Thus the antiarrythmic compounds of this invention may be administered to mammals, such as dogs, cats, etc., in pharmaceutical compositions, preferably in divided doses so that an average 70 kg. adult receives about 100 mg. (1.4 mg./kg.) to about 1000 mg. (14 mg./kg.) in a twenty-four hour period, preferably 200 mg. (2.8 mg./kg.) to 800 mg. (28 mg./kg.).

The invention is further illustrated by the following examples:

EXAMPLE 1

2,3,4,5-Tetrahydro-4,4-dimethyl-5-phenyl-1H-3-benzazepine

A solution of 6.6 g. (0.03 mole) of α-(1-amino-1-methylethyl)benzenemethanol and 4.8 g. (0.03 mole) of phenylacetaldehyde in 75 ml. benzene is refluxed for 1 hour while 0.7 ml. of water separates in a Dean-Stark trap. The infrared absorption spectrum showed absence of the C=O function and the presence of a C=N function at 1650 cm$^{-1}$. The solvent is removed in vacuo. The residue of the imino derivative was taken up with 60 ml. of methanol and 1.6 g. of KBH$_4$ is added with stirring at 20°-25° C. After 20 hours, the solution is evaporated in vacuo. The residue is taken up with cold water, and the resulting crystalline product (6.8 g., 85% crude yield, m.p. 103°-104° C.) is collected by filtration. Recrystallization from methanol gives pure α-{1-methyl-1-[(2-phenylethyl)amino]-ethyl}benzenemethanol as white crystals, m.p. 105°-106° C.

This product (13.5 g., 0.05 mole) is dissolved in 40 ml. of concentrated H$_2$SO$_4$ with external cooling and allowed to stand 48 hours at room temperature. The yellowish syrupy solution is poured onto crushed ice, made basic with NaOH and extracted twice with 200 ml. of ethyl acetate. The combined organic extracts are washed, dried (Na$_2$SO$_4$) and evaporated in vacuo. The residual cake is triturated with hot isopropanol to give, on cooling, 8.3 g. (66%) yield) of 2,3,4,5-tetrahydro-4,4-dimethyl-5-phenyl-1H-3-benzazepine as white crystals, m.p. 99°-100° C.

EXAMPLE 2

2,3,4,5-Tetrahydro-2,2,3-trimethyl-1-phenyl-1H-3-benzazepine

A solution of 2,3,4,5-tetrahydro-4,4-dimethyl-5-phenyl-1H-3-benzazepine (7.54 g., 0.03 mole) and 15 ml. of 36% aqueous formaldehyde in 25 ml. of 90% formic acid is refluxed for 8 hours. After the solution is concentrated to a low volume, ice and K$_2$CO$_3$ are added to pH 8.5 and extracted twice with 50 ml. of ethyl acetate. The combined organic extracts were washed, dried (Na$_2$SO$_4$) and evaporated to dryness in vacuo. Crystallization of the residue from isopropanol gives 6.0 g. (76% yield) of pure product as white crystals, m.p. 92°-93° C.

EXAMPLE 3

2,3,4,5-Tetrahydro-7,8-dimethoxy-2,2-dimethyl-1-phenyl-1H-3-benzazepine hydrochloride A solution of 8.3 g. (0.05 mole) of α-(1-amino-1-methylethyl)benzenemethanol, 9.8 g. (0.05 mole) of 3,4-dimethoxyphenylacetic acid and 13.6 g. (0.055 mole) of EEDQ (Aldrich Chem. Co.) in 300 ml. of tetrahydrofuran-ethanol is refluxed for 45 minutes and then allowed to stand for 20 hours at 25° C. The solution is evaporated in vacuo. The residue is taken up with 250 ml. of ethyl acetate, washed with dilute HCl, followed by washing with aqueous NaHCO$_3$. Subsequently, the extract is washed with aqueous NaCl, dried (Na$_2$SO$_4$) and evaporated to dryness in vacuo. Crystallization of the residue from ether gives 14.0 g. (82% yield) of pure 2-(3,4-dimethoxyphenyl)-N-(β-hydroxy-α,α-dimethylphenethyl)acetamide, m.p. 123°-124° C.

To a solution of this amide (12.0 g., 0.035 mole) is added 50 ml. of 1 molar solution of diborane in tetrahydrofuran dropwise over 30 minutes and allowed to stand for 24 hours. Hydrochloric acid (15 ml.) is added cautiously, and the solution is next briefly heated on a steam bath to destroy excess diborane. The solution is concentrated in vacuo to a low volume, made basic with NaOH at 0° C. and extracted twice with 200 ml. of ethyl acetate. The combined extracts are washed with aqueous NaCl, dried (Na$_2$SO$_4$) and concentrated to a low volume giving 9.5 g. (85% yield) of pure α-{1-1[(3,4-dimethoxyphenethyl)amino]-1-methylethyl}-benzyl alcohol, m.p. 125°-126° C.

The above amino derivative (8.2 g., 0.025 mole) is dissolved (with external cooling) in 30 ml. of conc. H$_2$SO$_4$ and allowed to stand at 25° C. for 48 hours. The syrupy solution is poured onto ice, made basic with NaOH and extracted twice with 175 ml. of ethyl acetate. The combined extracts are dried (Na$_2$SO$_4$) and evaporated in vacuo. To the residue is added 50 ml. absolute ethanol, and dry HCl is introduced to pH 2.5. After three days at 25° C., 8.1 g. (58% yield) of pure 2,3,4,5-tetrahydro-7,8-dimethoxy-2,2-dimethyl-1-phenyl-1H-3-benzazepine hydrochloride is obtained as white crystals, m.p. 286°-287° C.

EXAMPLE 4

2,3,4,5-Tetrahydro-2,2-dimethyl-1,5-diphenyl-1H-3-benzazepine

A solution of 19.1 g. (0.1 mole) of diphenylacetaldehyde and 16.5 g. (0.1 mole) of α-(1-amino-1-methylethyl)-benzenemethanol in 180 ml. of dry benzene is refluxed for 2 hours while 1.8 ml. water separates. The infrared spectrum shows the loss of the carbonyl function. After benzene is removed in vacuo, the residue is taken up with 150 ml. of methanol and treated (stirring) with 5.8 g. of KBH$_4$ for 5 hours at 25° C. The solution is concentrated to a low volume in vacuo. The mixture is treated with cold water and extracted twice with 150 ml. of ether. The combined extracts are washed, dried (Na$_2$SO$_4$) and evaporated. The residue is taken up with 60 ml. of chloroform and treated with dry HCl to pH 2.5 giving, after cooling, 16.8 g., m.p. 234°-235° C., decomposition. Further concentration of the mother liquor to a low volume gives 10.2 g. (68% overall yield) of additional product, m.p. 235°-236° C., decomposition. An analytical sample of α{1-[(2,2-diphenylethyl)-amino]-1-methylethyl}benzenemethanol hydrochloride is obtained by recrystallization from acetonitrile, m.p. 236°-237° C., decomposition.

This amino derivative (14.0 g., 0.037 mole) is added portionwise to 85 g. of polyphosphoric acid (preheated to 110° C.) over 45 minutes. Subsequently, the temperature is increased to 135° C. and maintained at this point for 3 hours to complete the cyclization. The contents are poured onto ice water, made basic with NaOH and extracted twice with 300 ml. of methylene chloride. The combined extracts are washed, dried (Na$_2$SO$_4$) and evaporated. Crystallization of the residue from isopropanol gives 9.9 g. (75% yield) of pure 2,3,4,5-tetrahydro-2,2-dimethyl-1,5-diphenyl-1H-3-benzazepine, m.p. 147°-148° C., decomposition.

EXAMPLE 5

3,4,5-Tetrahydro-2,2,3-trimethyl-1,5-diphenyl-1H-3-benzazepine

A solution of 6.0 g. (0.0184 mole) of 2,3,4,5-tetrahydro-2,2,3-trimethyl-1,5-diphenyl-1H-3-benzazepine and 20 ml. of 37% aqueous formaldehyde in 25 ml. of 70% formic acid is refluxed for 6 hours and then concentrated to a low volume. Ice is added; the mixture is made basic with $K_2CO_3$ and extracted twice with 100 ml. of ethyl acetate. The combined extracts are washed, dried ($Na_2SO_4$) and evaporated in vacuo. The solid residue is crystallized from isopropanol giving 5.6 g. (86% yield) of analytically pure white crystals, m.p. 137°-138° C.

EXAMPLE 6

2,3,4,5-Tetrahydro-7,8-dimethoxyl-1-(3-methoxyphenyl)-2,2-dimethyl-3-benzazepine hydrochloride A solution of 50 g. (0.26 mole) of 3,4-dimethoxyphenylacetic acid, 68 g. (0.28 mole) of EEDQ and 50 g. (0.26 mole) of α-(1-amino-1-methylethyl)-3-methoxybenzenemethanol in 450 ml. tetrahydrofuran are stirred for three days at 25° C., and then heated for 5 hours at 65° C. Tetrahydrofuran is evaporated in vacuo, and the residue is taken up with ice and 10% aqueous $H_2SO_4$ solution to pH 2. The amide is extracted twice with 500 ml. ethyl acetate. The combined organic extracts are washed with 500 ml. dilute aqueous $NH_4OH$ solution, dried ($Na_2SO_4$) and evaporated to dryness in vacuo. The residual oil is dissolved in hot diethyl ether from which it crystallizes to give 72.0 g. of impure product. Recrystallization from diethyl ether gives 70 g. (72% yield) of N-(β-hydroxy-3-methoxy-α,α-dimethylphenethyl)-3,4-dimethoxybenzeneacetamide as white crystals of analytical purity, m.p. 137°-138° C.

To a solution of 45 g. (0.12 mole) of N-(β-hydroxy-3-methoxy-α,α-dimethylphenethyl)-3,4-dimethoxybenzeneacetamide in 500 ml. dry tetrahydrofuran is added 200 ml. 1 M (0.2 mole) of $BH_3$/THF solution over 30 minutes at 0° C. with stirring. After addition, the reaction is allowed to stir overnight at room temperature. Water is added dropwise with caution until effervescence ceases, then 50 ml. more water is added all at once. Aqueous HCl (10%) is added to pH 1.0. Then the acidic reaction mixture is heated at 65° C. for 1 hour to remove most of the tetrahydrofuran and destroy excess $BH_3$. Next, the mixture is cooled with ice and basicified with $NH_4OH$. The mixture is extracted twice with 1 l. ethyl acetate. The combined organic extracts are dried ($Na_2SO_4$) and evaporated to dryness in vacuo. The crude hydrochloride is made by dissolving the residue in 250 ml. ethyl acetate and adding a solution of ethyl acetate saturated with dry HCl to pH 2.0. On standing, 25 g. of crude solid is obtained, which is recrystallized from 300 ml. hot isopropanol to give 18.5 g. (39% yield) of α-(1-{[2-(3,4-dimethoxyphenyl)ethyl]amino}-1-methylethyl)-3-methoxybenzenemethanol hydrochloride as a white crystalline solid of analytical purity; m.p. 185°-186° C.

Polyphosphoric acid (PPA) (75 ml.) is heated to 95° C. with stirring. After attaining 95° C., PPA is sufficiently fluid to allow addition of 17.5 g. (0.05 mole) α-(1-{[2-(3,4-dimethoxyphenyl)ethyl]amino}-1-methylethyl)-3-methoxybenzenemethanol portionwise while stirring. After 30 minutes at 95° C., the reaction is poured over ice and made basic with NaOH. The basic mixture is extracted twice with 500 ml. of ethyl acetate. The combined organic extracts are dried ($Na_2SO_4$) and evaporated to dryness in vacuo. The residue is dissolved in 150 ml. hot isopropanol, and isopropanolic HCl is added to pH 2.0. On standing at 25° C., the product crystallizes out of solution to give 9.8 g. (53% yield) of the white crystalline hydrochloride of analytical purity, m.p. 285°-286° C.

EXAMPLE 7

2,3,4,5-Tetrahydro-3,4,4-trimethyl-5-phenyl-1H-naphth[1,2-d]azepine

A solution of 74.5 g. (0.4 mole) of 1-naphthyl acetic acid, 111.0 g. (0.45 mole) of EEDQ and 66.0 g. (0.4 mole) of α-(1-amino-1-methylethyl)benzenemethanol in 1 l. tetrahydrofuran is stirred and heated for 2 hours at 65° C. and then allowed to stand for 20 hours at room temperature. THF is evaporated in vacuo, and the residue is taken up with ice and 10% aqueous $H_2SO_4$ solution to pH 2. The resulting amide is extracted twice with 750 ml. ethyl acetate. The combined organic extracts are washed with 500 ml. dilute $NaHCO_3$, dried ($Na_2SO_4$) and evaporated to dryness in vacuo. The oil is dissolved in 1 l. hot isopropyl ether and on standing at 25° C. gives 101.0 g. (77% yield) of N-(2-hydroxy-1,1-dimethyl-2-phenylethyl)-1-naphthaleneacetamide as an off-white crystalline solid of analytical purity, m.p. 106°-107° C.

To a solution of 41 g. (0.12 mole) of the above naphthaleneacetamide in 500 ml. dry tetrahydrofuran is added 175 ml. (0.175 mole) of $BH_3$/THF solution over 30 minutes at 0° C. with stirring. After addition, the reaction is allowed to stir overnight at room temperature. Following overnight stirring, water is added dropwise with caution until effervescence ceases, then 50 ml. more water is added all at once. Aqueous HCl (10%) is added to pH 1.0. The acidic reaction is next heated at 64° C. for 1 hour to remove most tetrahydrofuran and destroy excess $BH_3$, after which the mixture is cooled with ice and basicified to pH 10.0 with $NH_4OH$. The now basic mixture is extracted twice with 750 ml. ethyl acetate. The combined organic extracts are dried ($Na_2SO_4$) and evaporated to a low volume where scratching induces crystallization of about 30 g. of crude product. The crude product (10.0 g.) is purified by making the hydrochloride from isopropanol and isopropanolic HCl giving 8.5 g. of α-(1-methyl-1-{[2-(1-naphthalenyl)ethyl]amino}-ethyl)benzenemethanol hydrochloride as a white crystalline solid of analytical purity, m.p. 241°-242° C.

A solution of 10.0 g. of the impure base made above in 10 ml. 36% aqueous formaldehyde and 40 ml. 88% formic acid is refluxed for 15 hours. To the reaction mixture is added 10% aqueous HCl and heated on a steam bath for 45 minutes. The reaction mixture is next poured over ice and made basic with $NH_4OH$. The aqueous mixture is extracted twice with 250 ml. ethyl acetate. The combined organic extracts are dried ($Na_2SO_4$) and evaporated in vacuo to an amber oil which contains impure α-[1-methyl-1-({methyl[2-(1-naphthalenyl)ethyl]}amino)ethyl]benzenemethanol. This oil is refluxed in a $BF_3$/$Et_2O$ solution for 5 hours, then poured over ice and made basic with $NH_4OH$. The basic aqueous solution is extracted twice with 50 ml. ethyl acetate, and the combined organic extracts are dried ($Na_2SO_4$) and concentrated to a low volume (about 25 ml.) from which 2.5 g. 2,3,4,5-tetrahydro- 2,4,4-trimethyl-5-phenyl-1H-naphth[1,2-d]azepine crystallized as a white solid of analytical purity, m.p. 140°–141° C.

EXAMPLE 8

2,3,4,5-Tetrahydro-2,2-dimethyl-8-hydroxy-1-phenyl-1H-3-benzazepine

A stirred solution of 8.0 g (0.0268 mole) of α-(1-{[2-(4-methoxyphenyl)-ethyl]amino}-1-methylethyl)benzenemethanol in 30 ml of methanesulfonic acid is heated for 11 hrs. at 83° C. The brown solution is poured onto ice, made basic with NH4OH and extracted twice with 150 ml of ethyl acetate. The combined organic extracts are washed with saturated aqueous NaCl, dried (Na2SO4) and evaporated in vacuo. Trituration of the residue with hot acetonitrile and cooling gave 1.7 g (27%) of the above named 8-hydroxybenzazepine derivative as a result of cyclization with simultaneous cleavage of the methoxy function, mp 208°–209° C., dec. An analytical sample melting at 209°–210° C., dec., is obtained by recrystallization from acetonitrile.

We claim:

1. A compound of the formula

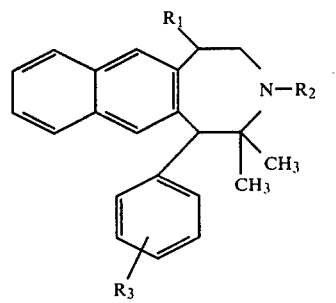

and pharmaceutically acceptable acid addition salts thereof wherein $R_1$ is hydrogen, lower alkyl, or phenyl, $R_2$ is hydrogen, lower alkyl or benzyl, $R_3$ is hydrogen, lower alkyl, chlorine or lower alkoxy.

2. The compound of claim 1 having the name 2,3,4,5-tetrahydro-3,4,4-trimethyl-5-phenyl-1H-naphth[1,2-d]azepine and pharmaceutically acceptable acid addition salts thereof.

* * * * *